Figure 1:
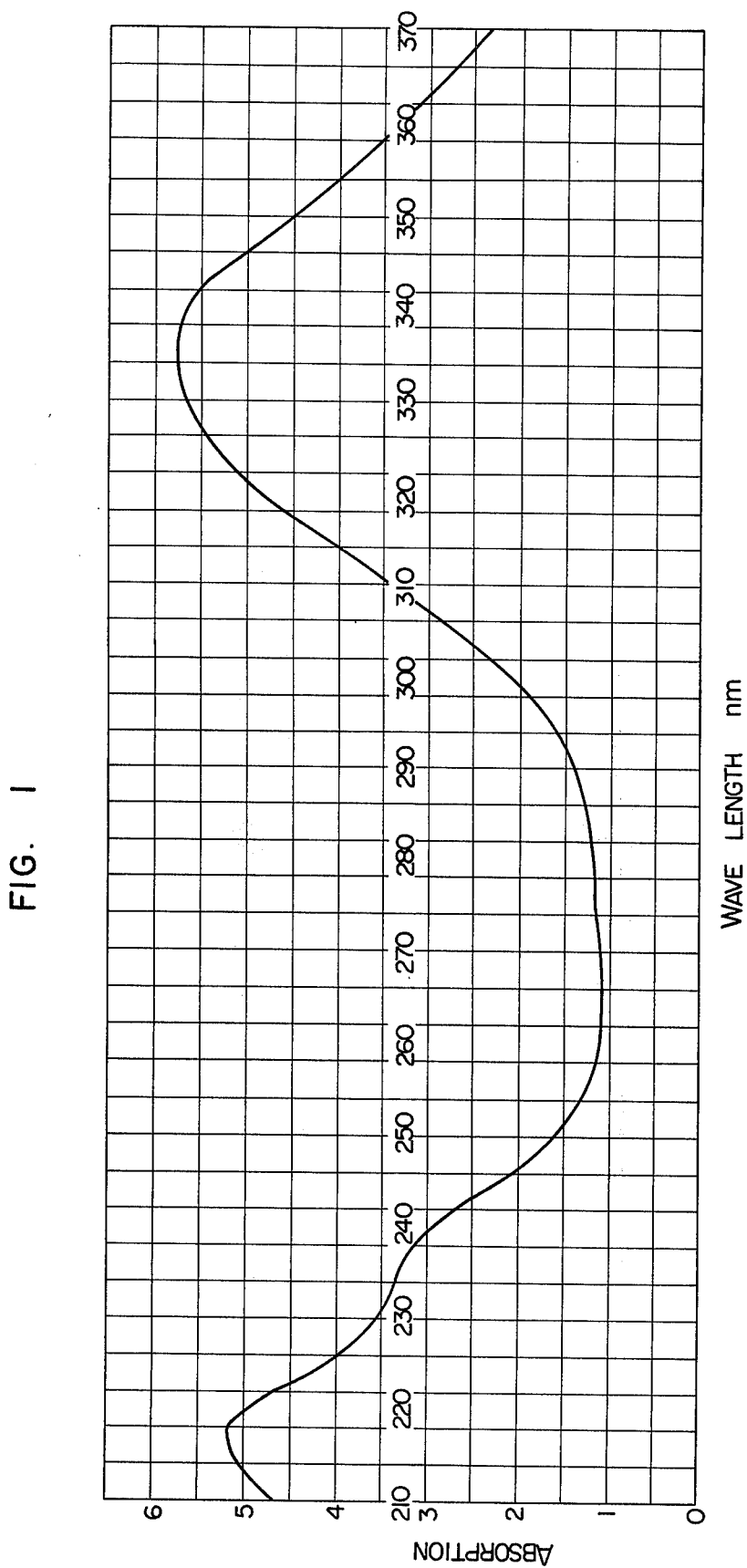

United States Patent [19]

Komatsu

[11] 4,011,140

[45] Mar. 8, 1977

[54] PROCESS FOR PRODUCING ANTITUMOR COMPOUND

[75] Inventor: Nobuhiko Komatsu, Tokyo, Japan

[73] Assignee: The Green Cross Corporation, Osaka, Japan

[22] Filed: Apr. 2, 1976

[21] Appl. No.: 673,056

[30] Foreign Application Priority Data

Dec. 25, 1975 Japan .............................. 50-155500

[52] U.S. Cl. ............................................ 195/80 R
[51] Int. Cl.$^2$ ............................................ C12D 9/00
[58] Field of Search .................................. 195/80 R

[56] References Cited
UNITED STATES PATENTS 3,361,742  1/1968  Berger et al. ..................... 195/80 R Primary Examiner—A. Louis Monacell
Assistant Examiner—Robert J. Warden
Attorney, Agent, or Firm—Cushman, Darby & Cushman

[57] ABSTRACT

A process for producing 5, 10, 11, 11a-tetrahydro-9,11-dihydroxy-8-methyl-5-oxo-1H-pyrrolo-[2,1-C][1,4]benzodiazepin-2-acrylamide, which comprises aerobicatlly culturing *Streptomyces spadicogriseus* KOMATSU, FERM P-3275, ATCC 31179, belonging to the genus Streptomyces to produce said compound in the nutrient medium, and recovering said compound from the medium. The compound thus obtained has an excellent antitumor activity.

16 Claims, 2 Drawing Figures

PROCESS FOR PRODUCING ANTITUMOR COMPOUND

This invention relates to a process for producing a 5-oxo-1H-pyrrolo[2,1-C][1,4]benzodiazepin-2-acrylamide compound having antimicrobial and antitumor activities and, more particularly, to a process for producing said compound by the fermentation procedure using a novel bacterium.

It has heretofore been known that 5,10,11,-11a-tetrahydro-9,11-dihydroxy-8-methyl-5-oxo-1H-pyrrolo[2,1-C][1,4]benzodiazepin-2-acrylamide having antitumor and antimicrobial activities and represented by the formula [I] is the fermentation products of strains belonging to the genus Streptomyces and the species *refuineus var. thermotolerans* [U.S. Pat. No. 3,361,742; Journal of American Chemical Society, 87, 5791-5793 (1965)].

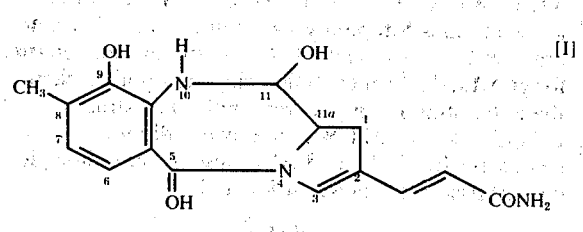

The present inventors found that a strain which belongs to the genus Streptomyces but is different from the above-noted known strains produces 5,10,11,11a-tetrahydro-9,11-dihydroxy-8-methyl-5-oxo-1H-pyrrolo-[2,1-C][1,4]benzodiazepin-2-acrylamide and, based on the finding, has now accomplished this invention.

An object of this invention is to provide a novel process for producing the compound of the formula [I].

The above object is achieved according to this invention by aerobicatlly culturing the genus Streptomyces and the species *spadicogriseus* KOMATSU, FERM P-3275, ATCC 31179, belonging to the genus Streptomyces to produce 5,10,11,11a-tetrahydro-9,11-dihydroxy-8-methyl-5-oxo-1H-pyrrolo[2,1-C][1,4]-benzodiazepin-2-acrylamide in the nutrient medium and recovering the compound from the medium.

The accompanying drawings represent the ultraviolet absorption spectrum (FIG. 1) and the infrared absorption spectrum (FIG. 2) of 5,10,11,11a-tetrahydro-9,11-dihydroxy-8-methyl-5-oxo-1H-pyrrolo-[2,1-C][1,4]benzodiazepin-2-acrylamide obtained according to this invention.

The conventionally known strains which produce the compound of the formula [I] are Streptomyces *refuineus var. thermotolerans*, NRRL 3143 and NRRL 3144, the morphological and physiological properties of which are described in detail in U.S. Pat. No. 3,361,742. The most distinctive feature of these strains is their thermophilic property, the optimum temperature for growth being in the range from 35° to 55° C; they hardly grow at 28° C or lower temperatures.

The strain [hereinafter referred to as FERM P-3275 (ATCC 31179)] used in this invention is an mesophilic bacterium which grows at a temperature in the range from 18° to 39° C, the optimum temperature being 25° to 38° C.

Bacteriological characteristics of FERM P-3275 (ATCC 31179) are as follows:

1. Morphological characteristics

The aerial and substrate mycelia developed well, branched and mature hyphae are about 1μ in width. The spore chains at the end of mature hyphae form into hooks, open loops or primitive spiral (Rectinaculum Apertum). When matured, spores are arranged in chains of more than 10. Electron micrographs of spores exhibit a having surface, the dimension of which are 1.51 - 1.58 μ by 0.9 - 1.1, the shape of which are oval.

2 Cultural characteristics on various culture media

Cultural characteristics of the present strain on various culture media after having been cultured at 28° C for 21 days is as shown in Table 1. The color designations are according to Nippon Shikisai Kenkyujo: "Standards of Color" (Nippon Shikisai Co., 1954).

Table 1

| Culture medium | Vegetative mycelium (Growth and reverse color) | Aerial mycelium | Soluble pigment |
|---|---|---|---|
| Czapek agar | Thin and scant; reverse color, light brown gray | Light brown gray | None |
| Glucose Czapek agar | Abundant and good; dull yellow changing to light brown gray | Powdery; light brown gray | Pale yellow |
| Glycerol Czapek agar | Abundant and very good; red brown in the initial stage of growth, turning to yellow brown with the progress of growth | Light brown gray changing to yellow brown | Pale yellow brown |
| Glycerol-asparagin agar (ISP No. 5) | Thin and scant; pale yellow changing to dark yellow | Brown white changing to pale yellow brown | None |
| Yeast extract malt extract agar (ISP No. 2) | Abundant and very good; grayish brown | Powdery; light brown gray | Pale yellow gray |
| Starch synthetic agar (ISP No. 4) | Abundant and good; pale yellow brown changing to light brown gray | Pale yellow brown changing to grayish yellow brown | None |
| Oat meal agar (ISP No. 3) | Thin but good; light brown gray | Powdery; pale brown | None |
| Tyrosine agar (ISP No. 7) | Thin and fair; light brown gray | Slightly powdery; light brown gray | None |
| Meat extract agar (ISP No. 8) | Thin and scant; pale yellow | Yellowish white | None |
| Glucose meat extract agar | Abundant and very good; light brown | Light brown gray | Pale yellow |
| Broth | Settling to the bottom: scant; yellowish white changing to pale yellow | Yellowish white changing to pale yellow | Pale yellow fading later |
| Glucose broth | Settling to the bottom; cells grown on the broth surface. | Yellowish white | Pale olive |

Table 1-continued

| Culture medium | Behavior on culture medium | | |
|---|---|---|---|
| | Vegetative mycelium (Growth and reverse color) | Aerial mycelium | Soluble pigment |
| Potato plug | wrinkled, dull yellow Very good; wrinkled; pale olive | Powdery; yellowish gray | Pale olive changing to olive gray |
| Carrot plug | Very good; wrinkled; olive changing to yellow brown | Powdery; pale yellow brown | None |
| Tryptone yeast extract (ISP No. 1) | Good; light brown gray | Light brown gray | None |
| Peptone yeast extract iron agar (ISP No. 6) | Good; light brown gray | Light brown gray | None |

3. Physiological properties

Conditions for growth:pH, 6.0 – 7.5; temperature, 18° – 39° C; aerobic.
Liquefaction of gelatin: pseudopositive.
Hydrolysis of starch: positive.
Formation of tyrosinase: negative.
Peptonization of milk: positive.
Coagulation of milk: negative.
Production of melanoid pigment: negative.
Reduction of nitrate: negative.
Decomposition of cellulose: negative.

4. Utilization of carbon sources

Utilization of carbon sources by the present strain is as follows:
1. Utilized: D-glucose, D-xylose, L-arabinose, D-fructose, D-galactose, D-mannitol.
2. Utilization doubtful: salicin.
3. Not utilized: D-rhamnose, raffinose, sucrose.

To summarize the above-noted characteristics, the present strain is an actinomycete characterized by producing 5,10,11,11a-tetrahydro-9,11-dihydroxy-8-methyl-5-oxo-lH-pyrrolo[2,1-c][1,4]benzodiazepin-2-acrylamide (hereinafter abbreviated as PBA); growth is generally good; reverse color is generally brown gray, sometimes pale yellowish; aerial mycelium is also brown gray in general, sometimes slightly yellowish; soluble pigment, if produced, is pale yellow brown, pale yellow or pale olive; causes hydrolysis of starch, peptonization of milk, and, although doubtful, liquefaction of gelatin.

As shown in Table 2, the present strain FERM P-3275 (ATCC 31179) differs distinctively from the known strains Streptomyces refuineus var. thermotolerans NRRL 3143 and 3144 in optimum temperature for growth, the former strain being mesophilic, whereas the latter strains being thermophilic. The strain FERM P-3275 (ATCC 31179), moreover, differs from the strains NRRL 3143 and 3144 also in morphological characteristics as shown in Table 3.

Table 2

| Strain | Optimal temperature for growth, ° C |
|---|---|
| FERM P-3275 (ATCC 31179) | 25 – 38 |
| Streptomyces refuineus var. thermotolerans NRRL 3143, 3144 | 35 – 55 |

Table 3

| Characteristics Strain | FERM P-3275 (ATCC 31179) | Streptomyces refuineus var. thermotolerans NRRL 3143, 3144 |
|---|---|---|
| Width of aerial mycelium | 0.9 – 1.3µ | 0.5 – 0.7µ |
| Morphology of spore | Chains: Open loops Hooks Primitive spiral | Coil |
| | Surface: Hairy | Warty |
| | Form: Oval (minor dia. 0.9 – 1.4 × major dia. 1.5 – 1.8)µ | Oval (minor dia. 0.5 – 1.2 × major dia. 1.0 – 2.3)µ |
| | Number: >10 | — |

By referring to "Bergey's Mannual of Determinative Bacteriology" (8 ed., 1974), taxonomic description of the present strain FERM P-3275 (ATCC 31179) is as follows: color of the aerial mycelium: gray; production of the melanoid pigment: negative; chains of spores: open, imperfect spiral (RA); spore surface: hairy. Accordingly, the strain belongs to the group 17; 42i. Utilization of carbon sources and produced antibiotics by the strain FERM P-3275 (ATCC 31179) and other strains belonging to the said group is summarized in Table 4.

Table 4

| Name of strain (Streptomyces) | None | D-glucose | D-xylose | L-arabinose | L-rhamnose | D-fructose | D-galactose | Raffinose | D-mannitol | i-inositol | Salicin | Sucrose | Fermentation product |
|---|---|---|---|---|---|---|---|---|---|---|---|---|---|
| calvus | − | + | + | + | + | + | + | + | + | + | + | + | Nucleocidin |
| cyanoalbus | − | + | + | + | + | + | + | + | + | − | − | + | |
| finlayi | | + | + | + | + | − | | − | − | − | − | ± | |
| flaveolus | − | + | + | + | + | + | + | + | + | + | + | + | Moenomycin |
| geysiriensis | | | | | | No description | | | | | | | |
| herbiferis | | + | + | + | + | | + | + | + | − | | + | |
| pactum | − | + | − | − | − | − | + | − | − | − | − | − | Pactamycin |
| spadicogriseus KOMATSU | − | + | + | + | − | + | + | − | + | − | ± | − | PBA |

For comparison, cultural characteristics of the above-noted strains which was compiled by reference to the following literature are summarized in Table 5:

1. Bergey's Manual of Determinative Bacteriology, 8. edition, 1974
2. ditto, 7. edition, 1957
3. K. H. Wallhausser et al., Antimicrobial Agents and Chemotherapy, 1965, 734 – 736
4. B. K. Bhuyan et al., ditto, 1961, 184 – 190

Table 5

| Strains | Cultural characteristics | Reference No. |
|---|---|---|
| FERM P-3275 (ATCC 31179) | Color of substrate mycelium is typically light brown gray; on some media, yellowish white or pale yellow. | — |
| Streptomyces calvus | Good growth on Czapek medium; formation of aerial mycelium is scant on most of the media. | (1) |
| Streptomyces cyanoalbus | Color of substrate mycelium is blue or green on some media. | (1) |
| Streptomyces finlayi | On some media, color of substrate mycelium changes from Green to yellow green. | (1) |
| Streptomyces flaveolus | Reverse color changes from yellow to dark yellow; aerial mycelium is light greenish gray; reverse color is white on synthetic agar medium, pale yellow on potato medium. | (2) |
| Streptomyces geysiriensis | No description was found on the color of substrate mycelium and aerial mycelium | (1), (3) |
| Streptomyces herbiferis | Color of substrate mycelium is dark yellow green on some media. | (1) |
| Streptomyces pactum | Color of substrate mycelium is from gray to grayish olive on most of the media and yellow or pale yellow on some media. | (4) |

From the above facts, the strain FERM P-3275 (ATCC 31179) was judged as a new species and given the name *streptomyces spadicogriseus* KOMATSU.

The procedure for culturing the present strain and the subsequent procedure for recovering the intended compound (PBA) of the formula [I] from the cultivation broth are carried out as mentioned below.

According to this invention, cultivation of the strain FERM P-3275 (ATCC 31179) is conducted in the presence of nutrient sources required by the strain and under the aerobic condition.

The necessary nutrient sources are selected by reference to the ingredients of various culture media mentioned before. For instance, as the carbon source, there may be used at least one of the glucose, xylose, mannitol, lactose, starch, dextrin, and molasses. For the nitrogen source, may be used at least one of the peptone, soybean meal, corn steep liquor, meat extract, dried yeast, cotton-seed cake, ammonium sulfate, and sodium nitrate. There may be added, if necessary, a suitable amount [about 0.05 to about 1.0% (w/v)] of inorganic salts of sodium, potassium, calcium, magnesium, iron, copper, zinc, and manganese. The concentration of carbon source in the medium is about 2 to about 10% (w/v) and that of the nitrogen source is about 0.1 to 2% (w/v). The designation of % (w/v) means a proportion of 1 g of solute in 100 ml of solution. The pH of the medium is about 6 to about 8, preferably 6.5 to 7.5. As a promoter for production of PBA, there may be added, optionally, organic and inorganic substances such as, for example, amino acids, e.g. cysteine, vatamins, and phosphates.

The fermentation is allowed to proceed under the aerobic condition at 25° to 35° C, preferably 30° to 35° C, by the technique of submerged culture, preferably with shaking or with agitation and aeration, although the plate culture is feasible. The cultivation period is usually 2 to 5 days. When the cultivation is carried out with shaking or with agitation and aeration, the maximum yield of PBA may be attained in a period of time as short as 3 to 5 days. Since the pH of the broth changes with the progress of fermentation, it is preferably adjusted by the addition of alkali or acid such as sodium hydroxide or hydrochloric acid so that a value of 6.0 to 8.0, preferably 7, may be maintained.

After completion of the fermentation, the broth is filtered and the objective compound is isolated from the filtrate. The isolation is effected by extraction with a solvent or by adsorption with an adsorbent or by the combination of these operations. The adsorbents for use in the selective adsorption of PBA from its aqueous solution are activated charcoal, silica gel, and the like. The objective compound is readily adsorbed on contact with the adsorbent and then eluted by use of alcohols or ketones which are miscible, at least partially, with water such as methanol, ethanol, butanol, acetone, and methyl ethyl ketone; mixtures of water and these alcohols or ketones; and halohydrocarbons such as chloroform, carbon tetrachloride, methylene chloride, and ethylene dichloride. The solvents for use in the extraction of PBA from its aqueous solution are those which are difficulty miscible with cold water, including alcohols such as butanols, pentanols, and hexanols; halohydrocarbons such as chloroform, carbon tetrachloride, methylene chloride, and ethylene dichloride; and mixtures of these solvents. These solvents are used in extracting the objective compound from not only the fermentation broth but also the aqueous solution of PBA, which is formed during the purification steps of PBA.

The solution in an organic solvent obtained from the fermentation broth by extraction or adsorption-elution is concentrated by evaporation or evaporated to dryness. The said concentrated solution in an organic solvent is subjected to chromatography to remove the impurities. The ultraviolet absorption spectrum can be employed for discriminating the fractions obtained by chromatography, since the objective compound shows a maximum absorption band at 330 – 335 nm. The fractions containing the objective compound are combined and recrystallization is carried out by use of a mixture of acetone (slightly soluble) and ethyl acetate (practically insoluble) or a mixture of acetone and water to obtain the pure objective compound of the formula [I].

The PBA thus obtained can be easily transformed into PBA methyl ether (ether formation at the position 11) and anhydro-PBA as shown in the following scheme:

The paths shown by arrows in the above scheme correspond to the following treatments: a, crystallization from a hot methanol-water mixture; b, crystallization from boiling acetone: c, crystallization from an acetone-water mixture at room temperature; d, heating under reflux in acetonitrile in the presence of a catalytic amount of Amberlite IRC-50 (an ion exchange resin of Rohm and Haas Co.) or heating under reflux in isopropenyl acetate [W. Leimgruber et al., Journal of American Chemical Society, 87 : 24, 5791 – 5793 (1965)].

PBA and the related compounds obtained as mentioned above show antitumor activity. Their physical and chemical properties shown in Table 6 coincide with those of the following substances disclosed in U.S. Pat. No. 3,361,742 and Journal of American Chemical Society, 87 : 24, 5791 – 5793 (1965):

PBA 5,10,11,11a-tetrahydro-9,11-dihydroxy-8-methyl-5-oxo-lH-pyrrolo[2,1-c][1,4]benzodiazepin-2-acrylamide.

Anhydro-PBA: 1,11a-dihydro-9-hydroxy-8-methyl-5-oxo-5H-pyrrolo[2,1-c][1,4]benzodiazepin-2-acrylamide.

PBA methyl ether: 5,10,11,11a-tetrahydro-9-hydroxy-11-methoxy-8-methyl-lH-pyrrolo[2,1-c][1,4]-benzodiazepin-2-acrylamide.

Table 6

| Item | PBA | Anhydro-PBA | PBA methyl ether |
|---|---|---|---|
| Melting point | 188° – 194° C | 203° – 206° C | — |
| Specific rotation | $[\alpha]_D^{25} + 930$ (c = 1, DMF) | $[\alpha]_D^{25} + 1793$ (c = 1, N,N-dimethylacetamide) | $[\alpha]_D^{25} + 999$ (c = 1, DMSO) |
| Elementary analysis: | $C_{16}H_{17}N_3O_4$ Calculated   Found | $C_{16}H_{15}N_3O_3$ Calculated   Found | $C_{17}H_{19}N_3O_4$ Calculated   Found |
| C | 60.92   61.07 | 64.62   64.44 | 61.81   61.72 |
| H | 5.44   5.32 | 5.09   5.19 | 6.06   6.18 |
| N | 13.33   13.13 | 14.14   14.10 | 12.73   12.60 |
| Molecular weight | 315 | 297 | 330 |

Figure 2:
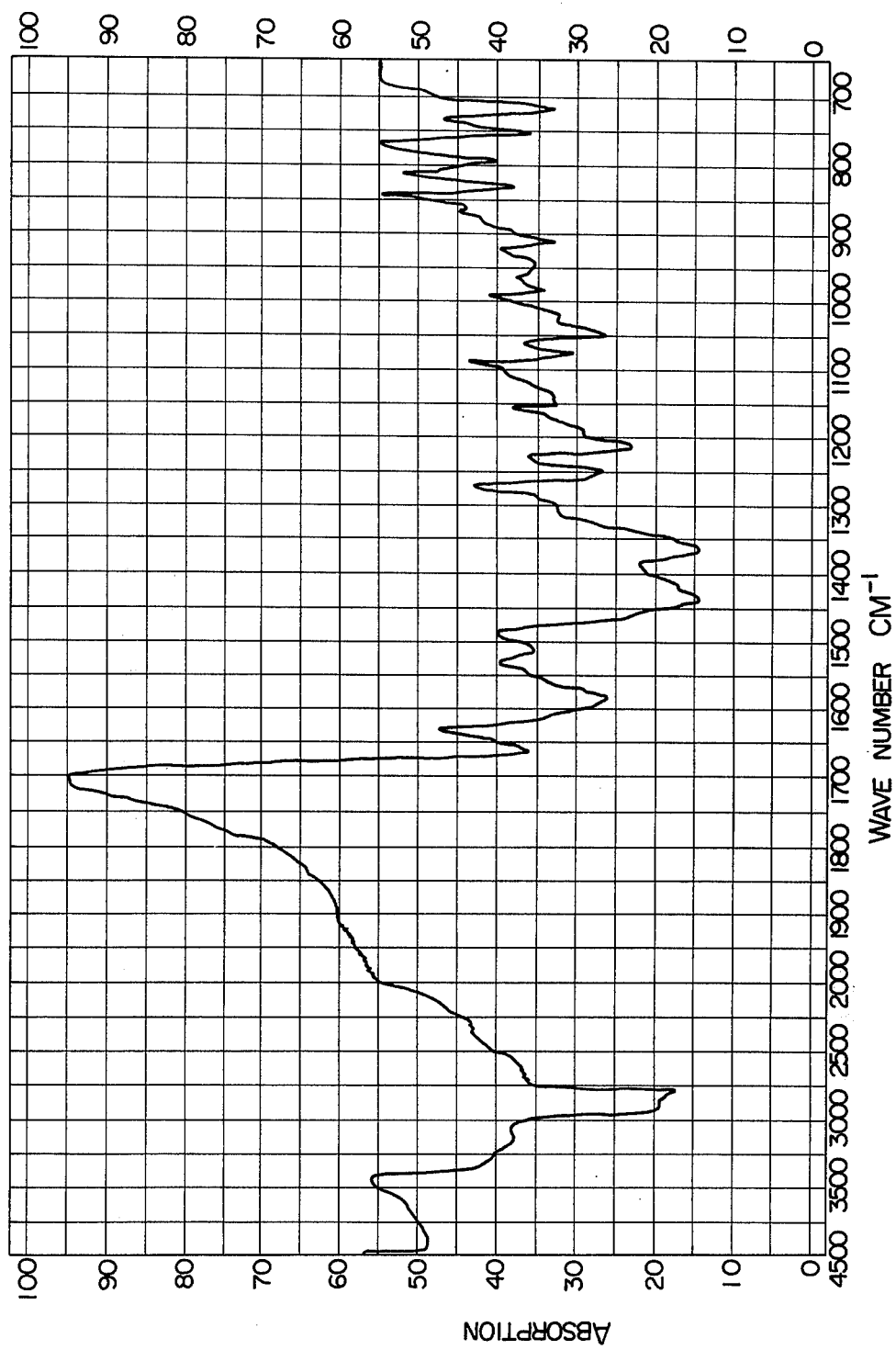

The ultraviolet absorption spectrum and the infrared spectrum of PBA are shown in accompanying FIG. 1 and FIG. 2, respectively.

The anti-tumor activities of PBA and related compounds were tested by mouse (dd strain, male, 18 – 22 g, a five-membered group for each test preparation)

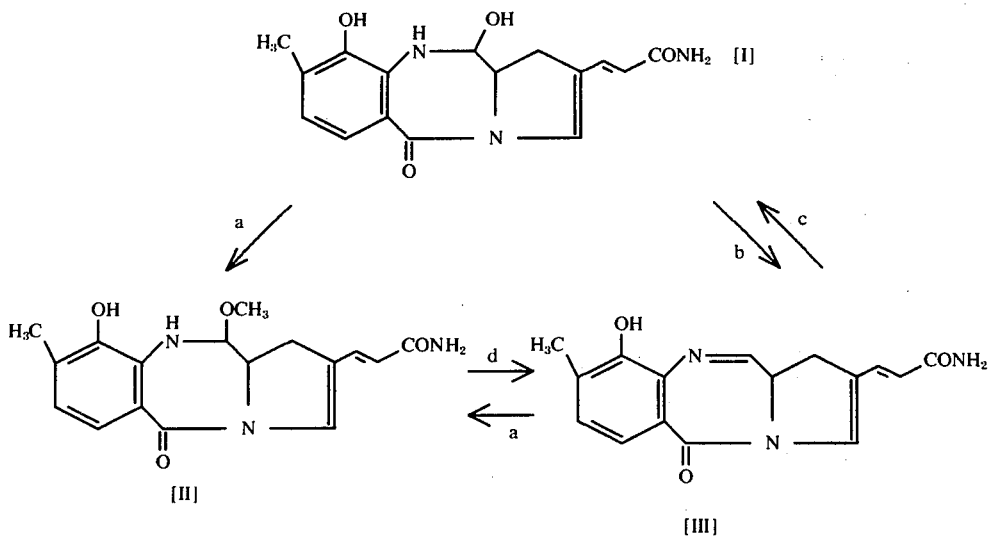

with ascites-type sarcoma 37, administering the prescribed dose of each test preparation into the abdominal cavity 5 times, starting on the day following the day of injection, and examining the ascites retention after 2 weeks. All of the test preparations were found active against the tumor as shown in Table 7, wherein, for comparison, test results with mitomycin and the control are also given.

Table 7

Antitumor activity of PBA and related compounds

| Test preparation | Dose, µg/kg/day | Ascites retention after 2 weeks (+: significant retention) |
|---|---|---|
| PBA | 30 | − |
| Anhydro-PBA | 30 | − |
| PBA methyl ether | 30 | − |
| Mitomycin | 200 | − |
| Control | − | + |

EXAMPLE 1

FERM P-3275 (ATCC 31179) was inoculated into 88 liters of a liquid medium (pH 7.0) containing 2% (w/v) of glucose, 0.5% (w/v) of meat extract, 0.5% (w/v) of peptone, and 0.5% (w/v) of common salt. The inoculated medium was cultivated in a 120-liter tank with agitation and aeration at 32° to 34° C for 2 days. The resulting fermentation broth containing multiplied cells was filtered to obtain 60 liters of filtrate. The filtrate was admixed with 0.3 kg of an activated charcoal. The activated charcoal bearing adsorbed PBA was collected by filtration and added into 3 liters of 80% aqueous acetone. After about one hour of agitation at room temperature, the active carbon was removed by filtration. The filtrate was concentrated under reduced pressure to about one-fifth of the initial volume. To the concentrate, was added 0.6 liter of butanol. After agitation, the butanol layer was separated, then concentrated to a syrupy state, and dissolved in a methanol-chloroform (1 : 9) mixture. The resulting solution was subjected to silica-gel column chromatography. Each fraction of the eluate was tested for intended constituent by ultraviolet absorption spectroscopy. The active fractions exhibiting a maximum absorption at 330 – 335 nm were combined and concentrated under reduced pressure to obtain a crude product. The crude product was dissolved in an acetone-ethyl acetate (1 : 1) mixture to form a saturated solution. The saturated solution was cooled to yield 2.52 g of purified PBA having the same physical and chemical properties and antitumor activity as those shown in Tables 6 and 7.

EXAMPLE 2

In the same manner as in Example 1, 65 liters of the filtrate of fermentation broth were obtained. By using a flash evaporator, the filtrate was concentrated to about one-fifth of the initial volume. To the concentrate was added 10 liters of butanol. After agitation, the butanol layer was separated. To the water layer was added another 5 liters of butanol. After agitation, the butanol layer was separated again. Both butanol layers were combined and concentrated to a syrupy state. The concentrate was dissolved in a methanol-chloroform (2 : 8) mixture and the resulting solution was subjected to silica-gel column chromatography. Each fraction of the eluate was tested for active constituent by ultraviolet absorption spectroscopy. The fractions exhibiting a maximum absorption at 330 – 335 nm were combined and concentrated under reduced pressure to obtain crude PBA (yellow powder). The crude PBA was dissolved in a 50% aqueous acetone to form a saturated solution. The saturated solution was cooled and filtered to obtain 2.12 g of a purified compound having the same physical and chemical properties and antitumor activity as those shown in Tables 6 and 7, respectively.

REFERENTIAL EXAMPLE 1

In one liter of methanol, was suspended 10 g of the crude PBA obtained in Example 1. The resulting suspension was heated at 50° C for 1 hour, then admixed with a small amount of an activated carbon, and filtered. The filtrate was concentrated under reduced pressure until commencement of crystallization and then left standing at −10° C to obtain PBA methyl ether having the same physical and chemical properties and antitumor activity as those shown in Tables 6 and 7, respectively.

REFERENTIAL EXAMPLE 2

In one liter of dehydrated acetone, was suspended 10 g of the crude PBA obtained in Example 1. The resulting suspension was heated at 45° C for 2 hours in a vessel provided with a condenser to prevent volatilization of the solvent. The resulting solution was concentrated to obtain precipitates. The precipitates were dissolved in 2,000 ml of acetonitrile, concentrated until commencement of precipitation, and left standing at −10° C to obtain anhydro-PBA having the same physical and chemical properties and antitumor activity as those shown in Tables 6 and 7, respectively.

I claim:

1. A process for producing 5,10,11,11a-tetrahydro-9,11-dihydroxy-8-methyl-5-oxo-lH-pyrrolo-[2,1-c][1,4]benzodiazepin-2-acrylamide (PBA), which comprises aerobically culturing Streptomyces spadicogriseus KOMATSU, FERM p-3275, ATCC 31179, to produce said compound in the medium, and recovering said compound from the medium.

2. A process according claim claim 1, wherein the medium is a nutrient source which is a carbon source and a nitrogen source.

3. A process according to claim 2, wherein the carbon source is at least one member selected from the group consisting of glucose, xylose, mannitol, lactose, starch, dextrin, and molasses.

4. A process according to claim 2, wherein the nitrogen source is at least one member selected from the group consisting of peptone, soybean meal, corn steep liquor, meat extract, dried yeast, cotton seed cake, ammonium sulfate, and sodium nitrate.

5. A process according to claim 2, wherein the concentration of the carbon source in the medium is 2 to 10% (w/v).

6. A process according to claim 2, wherein the concentration of the nitrogen source in the medium is 0.1 to 2% (w/v).

7. A process according to claim 1, wherein at least one of the inorganic salts of sodium, potassium, calcium, magnesium, iron, copper, zinc, and manganese is added to the medium.

8. A process according to claim 1, wherein an accelerator for the production of PBA is added to the medium.

9. A process according to claim 8, wherein the production accelerator is at least one member selected from the group consisting of amino acids, vitamins, and phosphates.

10. A process according to claim 1, wherein the cultivation is carried out at a pH of 6 to 8 and a temperature of 25° to 35° C.

11. A process according to claim 1, wherein the cultivation is carried out by the technique of plate culture, submerged culture, shaking culture, or aeration and agitation culture.

12. A process according to claim 1, wherein the cultivation is carried out for 2 to 5 days.

13. A process according to claim 11, wherein the cultivation is carried out for 3 to 5 days by the technique of shaking culture or aeration and agitation culture.

14. A process according to claim 1, wherein the product is obtained by filtering the fermentation broth, and isolating the product from the filtrate by extraction with a solvent, by adsorption with an adsorbent, or by combination of these operations.

15. A process according to claim 14, wherein the extraction solvent is at least one member selected from the group consisting of butanols, pentanols, hexanols, and halohydrocarbons.

16. A process according to claim 14, wherein the adsorbent is silica gel or activated charcoal.

* * * * *